United States Patent
Gourley (10) Patent No.: US 6,187,592 B1
(45) Date of Patent: Feb. 13, 2001

(54) METHOD FOR DETERMINING PROPERTIES OF RED BLOOD CELLS

(75) Inventor: Paul L. Gourley, Albuquerque, NM (US)

(73) Assignee: Sandia Corporation, Albuquerque, NM (US)

(*) Notice: Under 35 U.S.C. 154(b), the term of this patent shall be extended for 0 days.

(21) Appl. No.: 09/221,331

(22) Filed: Dec. 23, 1998

(51) Int. Cl.⁷ ...................................................... G01N 33/72
(52) U.S. Cl. ........................... 436/66; 436/164; 356/318; 356/339; 356/40
(58) Field of Search ............................... 436/63, 66, 164; 422/82.5, 82.09; 356/318, 338, 339, 301, 246, 39, 40, 436, 440

(56) References Cited

U.S. PATENT DOCUMENTS

| | | | |
|---|---|---|---|
| 4,199,748 | 4/1980 | Bacus | 340/146.3 |
| 5,194,909 | * 3/1993 | Tycko | 356/40 |
| 5,360,739 | * 11/1994 | Fan | 436/63 |
| 5,608,519 | * 3/1997 | Gourley | 356/318 |
| 5,686,309 | 11/1997 | Frank et al. | 436/66 |
| 5,773,301 | * 6/1998 | Zeigler | 436/66 |
| 5,793,485 | 8/1998 | Gourley | 356/318 |
| 5,817,519 | * 10/1998 | Zelmanovic et al. | 436/63 |
| 5,999,259 | * 12/1999 | Atkinson | 356/347 |
| 6,025,201 | * 2/2000 | Zelmanovic et al. | 436/63 |

FOREIGN PATENT DOCUMENTS

0616791 * 9/1993 (EP).

OTHER PUBLICATIONS

Gourley et al (Advances in laser and light spectroscopy to diagnose cancer and other diseases II: Optical Biopsy, Proc Biomedical Optics Society, 1995, SPIE vol. 2387:148–161).*

* cited by examiner

Primary Examiner—Lyle A. Alexander
(74) Attorney, Agent, or Firm—George H. Libman (57) ABSTRACT

A method for quantifying the concentration of hemoglobin in a cell, and indicia of anemia, comprises determining the wavelength of the longitudinal mode of a liquid in a laser microcavity; determining the wavelength of the fundamental transverse mode of a red blood cell in the liquid in the laser microcavity; and determining if the cell is anemic from the difference between the wavelength of the longitudinal mode and the fundamental transverse mode. In addition to measuring hemoglobin, the invention includes a method using intracavity laser spectroscopy to measure the change in spectra as a function of time for measuring the influx of water into a red blood cell and the cell's subsequent rupture.

9 Claims, 5 Drawing Sheets

Wavelength

METHOD FOR DETERMINING PROPERTIES OF RED BLOOD CELLS

STATEMENT OF GOVERNMENT INTEREST

The United States Government has rights in this invention pursuant to Department of Energy Contract No. DE-AC0494AL85000 with Sandia Corporation.

CROSS REFERENCE TO RELATED APPLICATIONS (Not Applicable)

BACKGROUND OF THE INVENTION

Different properties of blood provide information on the condition of the blood's provider. For example, anemia is a reduction in total circulating red blood cell mass, diagnosed by a decrease in hemoglobin concentration. In addition, a variety of detrimental red blood cell conditions such as hereditary spherocytosis and thalassemia are indicated by fragile blood cell membranes. Measuring these properties has historically taken relatively large samples of blood and time. This invention reduces both the sample size and the time for property determination.

According to E. Uthman, *Understanding Anemia*, University of Mississippi Press, Chapter 1, 1998, red blood cells (RBCs) are oxygen transporters. They are basically membrane structure filled with hemoglobin (a 33% solution). This pigmented protein accounts for both their natural red color and affinity for acidic dyes, such as eosin. They retain a cytoskeleton which gives them distinctive biconcave architecture. RBCs are also highly flexible and resilient, which is important for passage through capillary lumens. The shape of the red cell is referred to as a biconcave disc. (A donut with its hole partially filled in is a good analogy.) Red blood cells are about 7.5 $\mu$m in diameter and 2–3 $\mu$m in thickness, but they must be pliable enough to squeeze through smaller capillaries at high velocity. The critical importance of cytoarchitecture is highlighted by diseases such as sickle cell anemia in which RBC shape is distorted, resulting in blocked capillaries and frequently breakage (hemolysis) of the fragile sickle shaped cells.

Estimates suggest that 20% of the world's population suffers from various anemias arising from dietary or genetic deficiencies. Anemic patients have low oxygen-carrying capacity of the blood, with resultant tissue hypoxia. The clinical symptoms are related to the severity of the anemia, and may include pallor, tachycardia, angina, light-headedness and fatigue. Anemia may be due to increased blood loss, decreased red blood cell production (hypoproliferative anemia), or increased red blood cell destruction (hyperproliferative anemia).

Hemoglobin is a protein that serves as a carrier for oxygen from the lungs to the tissues. To work properly, the hemoglobin has to hold on to oxygen molecules with just the right amount of force. If the hemoglobin molecule binds the oxygen molecules too loosely, then it will not be capable of picking them up at the lungs. If it binds the oxygen too tightly, then when it gets out to the tissues it will not release the oxygen to the tissues that need it. Hemoglobin has to have its peculiar structure for proper oxygen transport, even if that structure turns out to be very delicate. Almost any type of natural or artificial toxic substance can cause the hemoglobin molecule to denature (be permanently altered so that it does not work).

According to the *Merck Manual*, 16$^{th}$ ed, 1992, anemia results from one or more combinations of 3 basic mechanisms: blood loss, decreased RBC production, or increased RBC destruction (hemolysis). For diagnosis of anemia, once blood loss is ruled out, only the other 2 mechanisms remain. Since RBC survival is 120 days, maintenance of steady populations requires renewal of 1/120 of the cells each day. Complete cessation of RBC production results in a decline of about 10%/wk (1%/day) of their initial number. When RBC values fall>10%/wk (ie, 500,000 RBC/$\mu$L) without blood loss, hemolysis is established as a causative factor.

The presence of anemia is typically detected with a blood count that is historically made by mixing a measured volume of blood with an appropriate diluent or lysing agent and counting RBCs in a chamber under the microscope. There have been many systems deviced to automate this procedure.

U.S. Pat. No. 4,199,748 of J. Bacus discloses a system for diagnosing anemia by imaging a number of cells and determining characteristics based on cell shape.

U.S. Pat. No. 5,194,909 of D. Tycko discloses a system for measuring hemoglobin concentration from a stream of individual, spaced-apart cells passing through a flow chamber.

U.S. Pat. No. 5,686,309 of R. Frank et al. discloses a system for determining hemoglobin content by measuring the electrical parameters of individual red blood cells.

U.S. Pat. No. 5,793,485 of P. Gourley, *Resonant-Cavity Apparatus for Cytometry or Particle Analysis*, discloses a resonant-cavity apparatus for analyzing cells which includes a cavity formed by at least two spaced reflecting mirrors that contains a semiconductor gain medium and an analysis region for containing one or more cells or particles to be analyzed. At col. 17, lines 1–30, the patent discusses how the emission spectrum of the light beam through the cavity can be used to recover information about the size and shape of a cell or particle, or components of the cell or particle, in the cavity. However, there is no teaching in this earlier work of this invention.

According to Ian Russell, Delmar's Clinical Laboratory Manual Series: Hematology, Delmar Publishers, New York 1997, most routine blood cell analysis such as blood counts are carried out with automated instrumentation. Accordingly, many modern laboratories do not prepare manual differential slides on all blood samples. However, manual differential provides information that a computerized count could not, such as specific red cell morphology, platelet morphology, and presence of inclusion bodies. When any results are abnormal in the automated cell count, a differential slide is often made. However, this process is labor intensive and time consuming.

An important feature of red blood cells is osmosis and membrane permeability, the ability of membranes to selectively transport fluids. The cells are freely permeable to water and anions like Cl$^-$ and HCO$_3^-$ but nearly impermeable to cations like Na$^+$ and K$^+$, so the cell maintain volumes and homeostasis. Integral membrane pumps driven by Adenine Triphosphate (ADT) transport Na$^+$ out and K$^+$ into the cell, respectively.

If red blood cells are placed in an isotonic (therefore isosmotic) solution, they will be in osmotic equilibrium and the cells will neither swell and burst (lyse) nor shrink (crenate). However if the cell membrane is permeable to the solute and initially there is a decreasing concentration gradient from outside to inside the cell, solute will diffuse into the cell and add to the solute already present there. Eventually the osmotic potential of the cytosol will be greater than the osmotic potential outside and the bathing solution will have become hypotonic. The natural consequence is for osmosis to occur, for water to diffuse into the cell, producing lysis. In lysing red blood cells, the biconcave shape changes to spherical and the membrane ruptures. The time it takes for lysis to occur is an indirect function of permeation rate. The physical rupture of the bilipid membrane under tension has been analyzed theoretically and found to be a thermally activated process.

The biocavity laser of this invention can eliminate much expensive testing by providing a more thorough analysis of blood cell morphology, especially for the determination of cell size, shape, and distribution in a large population.

SUMMARY OF THE INVENTION

To achieve the foregoing and other objects, and in accordance with the purpose of the present invention, as embodied and broadly described herein, the present invention may comprise a method for quantifying anemia comprising determining the wavelength of the longitudinal mode of a liquid in a laser microcavity; determining the wavelength of the fundamental transverse mode of a red blood cell in the liquid in the laser microcavity; and determining if the cell is anemic from the difference between the wavelength of the longitudinal mode and the fundamental transverse mode.

In addition to measuring hemoglobin, the invention includes a method for measuring lysing, (which is typically the influx of water into red blood cells) and subsequent cell rupture by using intracavity laser spectroscopy. The technique uses the decrease in cell refractive index due to dilution of hemoglobin in the cell. Microscopic observation of cells under a coverslip (the conventional technique) requires many seconds for the cell to be substantially lysed. Using the microcavity as taught by this invention, refractive changes due to the influx of water can be observed within tens of milliseconds, providing an indication of very early stages of osmosis.

Additional objects, advantages, and novel features of the invention will become apparent to those skilled in the art upon examination of the following description or may be learned by practice of the invention. The objects and advantages of the invention may be realized and attained as particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principles of the invention.

FIG. 2b shows a schematic top view of the embodiment of FIG. 2a.

DETAILED DESCRIPTION OF THE INVENTION

Figure 1:
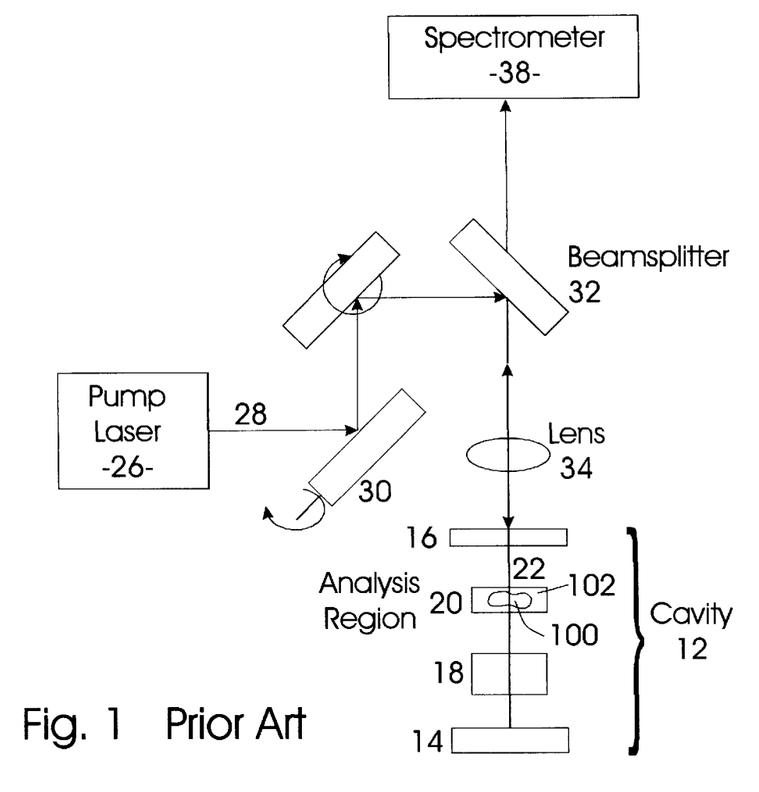
FIG. 1 shows an overall view of the apparatus for practicing this invention.

The apparatus which may be used in the practice of this invention is shown in FIG. 1, which duplicates FIG. 1 of the previously referenced U.S. Pat. No. 5,793,485, which patent is incorporated herein by reference thereto. A microcavity spectrometer 10 includes a resonant optical cavity 12 formed by at least two reflecting mirrors (e.g. a lower mirror 14 and and upper mirror 16), a gain medium 18 within the cavity, and an analysis region 20 within the resonant optical cavity 12 for locating at least one blood cell 100 to be analyzed. Pump means are provided for activating the gain medium 18 for generating optical gain within the cavity for emission of a light beam 22 (either a spontaneous emission beam or a laser beam). Alternatively, the lower mirror 14 and gain medium 18 may consist of a semiconductor diode with electrical injection, so the pump laser can be eliminated. Microcavity spectrometer 10 further comprises analysis means such as a photodiode spectrometer 38.

Figure 2A:
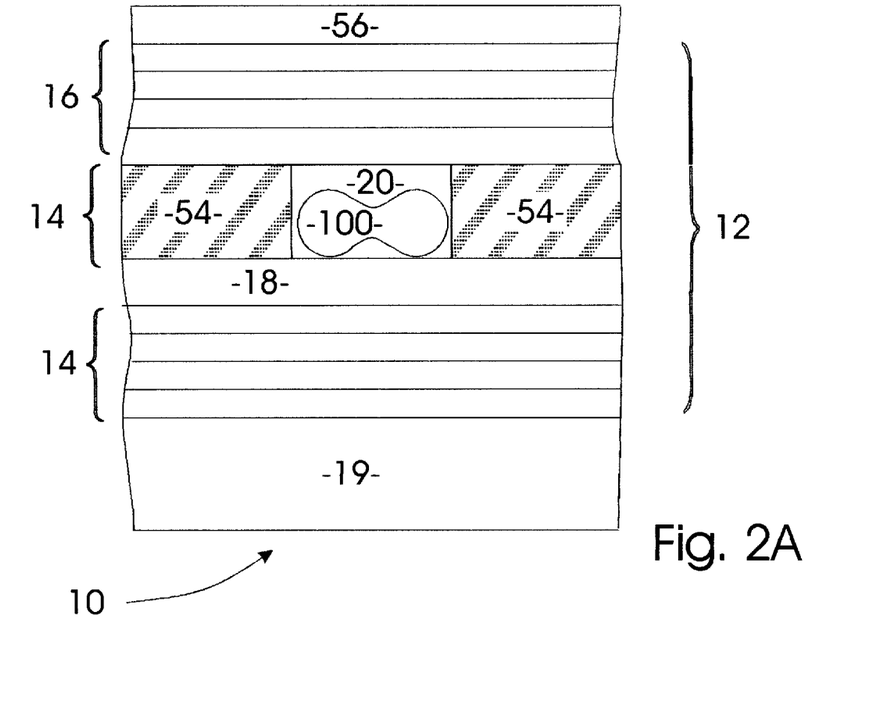
FIG. 2a shows a preferred embodiment of the microcavity of the invention.

In a preferred embodiment shown in FIG. 2A, mirror 14 and gain region 18 may be grown on a semiconductor wafer 19 and form a laser gain region atop a multilayer reflector. The other mirror 16 may be a dielectric multilayer on a substrate 56. Patterned insulating layer 54 has a channel extending through the device forming analysis region 20 for containing the blood cell 100 under test. The width of region 20 may be on the order of 10 microns and have a thickness on the order of 3 microns.

Figure 2B:
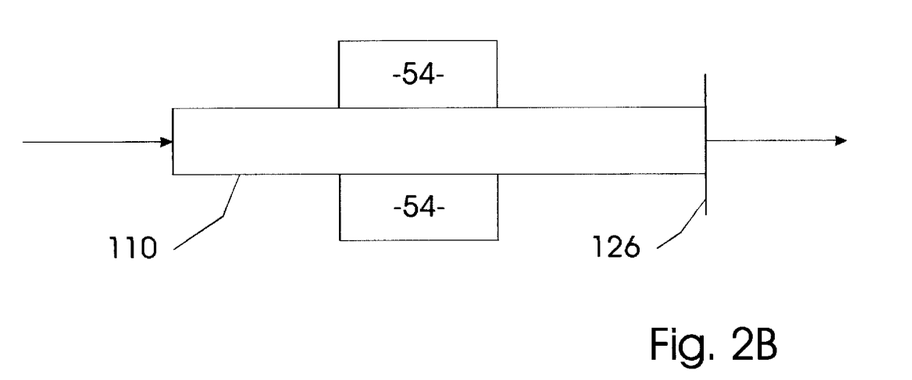

An advantage of this embodiment is that the blood under test may flow through the cavity to provide an efficient way to quickly measure a number of individual cells. As shown in FIG. 2B, an enclosed tube 110 leads into and out of analysis region 20. Blood to be tested is applied under a positive pressure from the input end. A gate 120 at the output end controls the flow through tube 110 and region 20. By closing gate 120, an individual cell may be stopped in region 20. By opening gate 120, this cell will move out and another permitted to take its place. The relatively narrow width of region 20 ensures the placement of each serially travelling cell within the path of beam 22 for the measurement.

Figure 3:
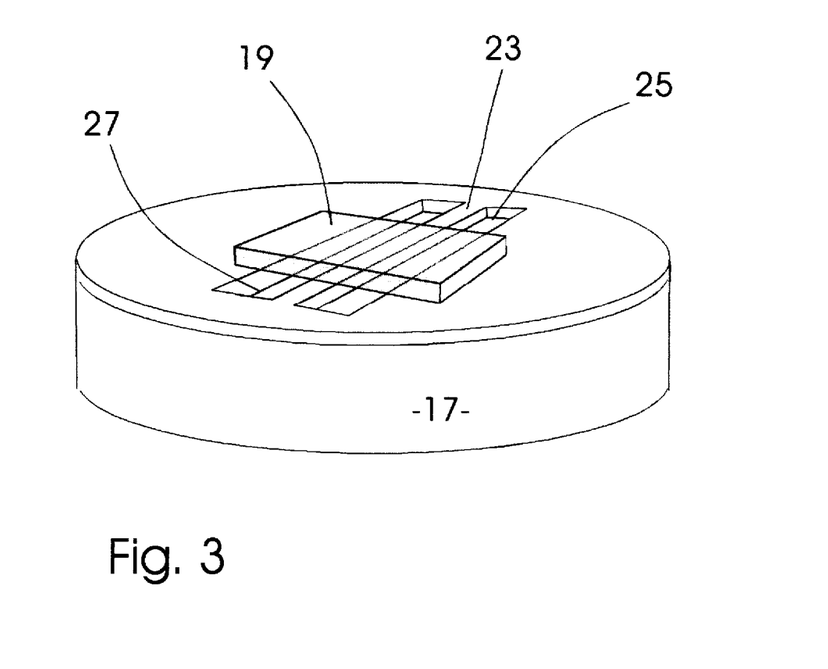
FIG. 3 shows an alternative embodiment of the invention.

An alternative embodiment is shown in FIG. 3 to have a semiconductor mirror atop a glass substrate 17. The glass surface is micromachined to define surfaces or channels for transporting fluids. For example, a wicking microbridge 23 may be formed by machining two slots 25, 27 into the glass surface and contacting it to a cleaved semiconductor rectangle 19 as shown in FIG. 2. The dimensions of the rectangle are about 5 mm and are less than the length of the glass slots. Thus, the glass surface between the slots is exposed outside the contact area of the semiconductor. The optical contact between the microbridge and semiconductor surface leaves a small air gap that can be controlled by pressure from 0 to several microns. The gap is set by bonding the wafer along its perimeter to the glass surface. The gap dimension of the resulting assembly is then assessed by viewing the bridge region through the glass substrate. In use, fluid placed on the microbridge adjacent the end of semiconductor 19 is wicked along the microbridge for analysis. Lysing material such as water that is placed in a slot is also wicked into the microbridge.

Figure 4A:
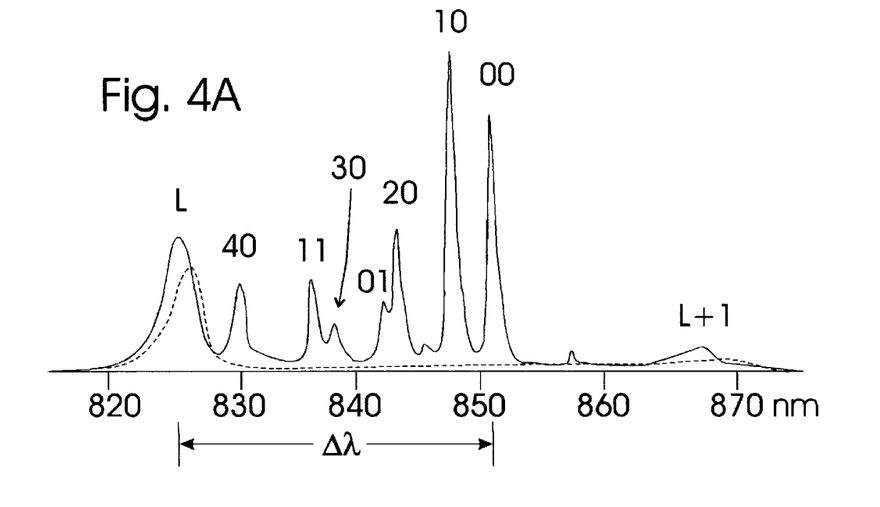
FIGS. 4a and 4b each show the spectrum for a cavity with and without a sample of normal red blood cells.
Figure 4B:
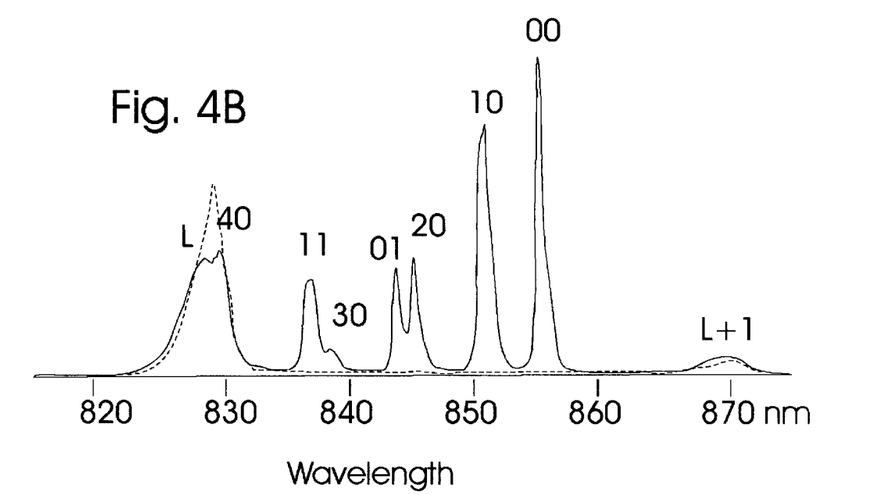

The microcavity serves as an optical waveguide to confine light generated in the resonator by the semiconductor. The waveguiding effect is due to slight differences in the dielectric constants between various cell components and the surrounding fluids. The laser operates at resonant frequencies established by the dielectric properties of the cells. By using a high resolution spectrometer, these lasing frequencies can be resolved into narrow spectral peaks. The spacing and intensity distribution between peaks provides a unique spectral signature for each different cell as shown in FIGS. 4a and 4b for two samples of red blood cells.

When no cell is present, the cavity resonance frequencies will be established by the cavity length L and the dielectric constant of the fluid in the cavity. The longitudinal mode wavelengths are $$\lambda_l = \frac{\xi}{(l - \phi/2\pi)} \quad (2)$$

where l is the longitudinal mode index and $\Phi$ is the sum of mirror phases and $\zeta = 2\Sigma l_i n_i$ is the roundtrip optical pathlength in the cavity comprising a sum of lengths $l_i$ of index $n_i$, (typically a fluid region and a semiconductor gain region). The longitudinal mode separation or free spectral range is given by $$\frac{\Delta\lambda_l}{\lambda_l} = -\left(\frac{\lambda_l}{\xi}\right)\left[1 + \frac{\lambda_l \xi'}{\xi} + \frac{\lambda_l^2 \phi'}{2\pi\xi}\right] \quad (3)$$

where primes denote derivatives with respect to wavelength. For a fluid of index $n_1$, equation 2 can be rewritten as the bare-fluid mode wavelength $\lambda_1 = 2L^* n_1/l$, where $L^*$ is an effective length of the cavity. The dashed curves in FIGS. 4a and 4b illustrates the longitudinal mode for the cavity of FIG. 2 or FIG. 3 without the cell.

To first order, a cell in the cavity can be modeled by a disk of index $n_2$ surrounded by a fluid of index $n_1$. This problem is similar to the solution of optical modes in a dielectric waveguide and has been discussed in P. Gourley et al., *Surface-emitting Semiconductor Laser Spectroscopy for Characterizing Normal and Sickled Red Blood Cells*, Advances in Laser and Light Spectroscopy to Diagnose Cancer and Other Diseases II: Optical Biopsy, Proc. Biomedical Optics Society, SPIE vol. 2387, 148–161 (March 1995). In this case, the cell will perturb each bare-fluid mode by adding a series of modes at longer wavelengths $\lambda_{lmn}$ where the indices l, m, and n correspond to the axial, radial, and azimuthal solutions to the wave equation for light confined by the cell in the cavity.

The fundamental transverse mode has the longest wavelength separation from the bare-fluid mode 00 $\lambda_1$ of the cavity and is given to good approximation by $$\Delta\lambda_{lmn} = \Delta\lambda_l - \frac{\lambda_l^3 x_{00}^2}{2\pi^2 n_2^2 d^2} \quad (4)$$

where d is the cell diameter and the first term arises from the dielectric shift $\Delta\lambda_l = \Delta\zeta/(1-\Phi/2\pi)$, where $\zeta = 2\Sigma l_{l\Delta ni}$, due to the change in index from the fluid (blood plasma) to that of the cell. The second term arises from the lateral confinement of light by the cell, and has a calculated value for red blood cells of 1.8 nm. The calculated value for platelets is about 9 nm. Experimentally, it is observed that $\Delta\lambda_{lmn} \approx 20$ nm for red blood cells, so the primary cause of the change is the index shift.

The solutions for the fundamental and higher order transverse modes are solutions to the wave equation and are given by the characteristic equations $$\frac{XJ_{m\pm1}(X)}{J_m(X)} = \pm Y K_{m\pm1}\frac{(Y)}{K_m(Y)} \quad (5)$$

and $$X^2 + Y^2 = V^2 \quad (6)$$

where J and K are Bessel and modified Bessel functions, respectively, Successive longitudinal modes L and L+1, and transverse modes 40, 11, 30, 01, 20, 10 and 00 for mode L, are shown in FIGS. 4A and 4B and X=ka and Y=λa are wavevector parameters of the cell and surrounding regions, respectively. The optic parameter $$V = \left(\frac{2\pi a}{\lambda_l}\right)(n_2^2 - n_1^2)^{1/2}$$

where a is the cell radius and the latter factor is the numerical aperture of the cell.

Each mode corresponds to an eigenfrequency of the resonator. The free space spectral wavelengths are given by $$\lambda = \frac{2\pi n_1}{\left([(X_{mn}/d)^2 + (l\pi/L*)^2]\right)^{1/2}} \quad (7)$$

where $X_{mn}$ is the $n^{th}$ root of equation 5. The set of roots includes the fundamental mode of equation 4 which is derived from equation 7 in the limit $(l\pi/L^*) >> X_{mn}/d$, and shorter wavelength modes up to a limit set by $X_{mn} \approx V$. At this cutoff condition, equations 7 becomes $$\lambda_{min} = \frac{2\pi n_1}{\left([(2\pi/\lambda_1)^2(n_2^2 - n_1^2) + (l\pi/L*)^2]\right)^{1/2}} \quad (8)$$

but $l\pi/L^* = 2\pi n_1/\lambda_1$, so that $\lambda_{min} = \lambda_l$.

The total number of modes, including 2 polarizations and 2 helicities, is given by $M_t \approx (4V^2/\pi^2) + 2$. For typical red blood cells with 7 $\mu$m diameter (in typical experiment with whole blood diluted in 50:50 in isotonic solution), index $n_2 = 1.390$ and $n_1 = 1.335$ at 850 nm, and V=10, so about 40 total modes are present. Experimentally, it is found that modes of different polarization and helicity are nearly or exactly degenerate, respectively. Thus, the number of distinctly observable modes is $M_{ob} \approx V^2/\pi^2 \approx 10$ for red blood cells. For blood platelets of 3 $\mu$m diameter and $n_2 = 1.37$, $V \approx 3.4$ and $M_{ob} \approx 1$. For white blood cells of diameter 12 $\mu$m and $n_2 = 1.37$, $V \approx 14$ and $M_{ob} \approx 20$. Experimentally, red cells are observed to have 7–9 modes, platlets have 1–2 modes, and white cells have 15–30 modes. FIG. 4a shows about 8 modes for a red blood cell. Thus, the disk model is reasonably accurate for describing the transverse modes in cells.

A single cell has about $10^9$ hemoglobin molecules, and the protein hemoglobin constitutes 95% of the red blood cells dry weight. In normal hydrated cells, the concentration of hemoglobin is in the range 32 to 36 g/dL. In anemic individuals these level dip to half these values or even less in severe cases. In the microcavity, the waveguiding property of the cell is a function of the refractive indices of the cell, which is primarily determined by the hemoglobin concentration, and the surrounding fluid, which is primarily blood plasma, i.e., water with some proteins and electrolytes.

R. Barer, J. Opt. Soc. Am. 47, 545–52 (1957), has shown a linear relationship between the index and the molecular concentration as $$n = n_0 + \alpha C \qquad (9)$$

where $n_0$ is the index of the solvent, $\alpha$ the specific refractive increment of the molecule, and C the concentration in grams per 100 ml. A literature value for $\alpha$ of hemoglobin is 0.00193 at 586 nm. Thus, a normal red blood cell concentration of 34 g/dL gives an index $n = n_0 + 0.0656$. The values of $n_0$ for blood plasma and water at 850 nm are 1.342 and 1.330, respectively.

From equation 9, mode spectral shift $\Delta\lambda_m$ of a microcavity loaded with a red blood cell may be shown to be $\Delta\lambda_m/\lambda_m = \Delta n_1/(n_1 + l_2 n_2/l_1)$, where $\Delta n_1 = \alpha C$ is the change in cell index, and the term in brackets is a spatial weighting of the optical intensity due to the relative thickness of the cell $l_1$ and an internal cavity length $l_2$ of index $n_2$. For a normal red blood cell, typically, $l_1 = 2.5$ μm and $l_2 = 1.4$ μm, $n_2 = 3.1$, so $\Delta\lambda_m/\lambda_m = 0.021$ and $\Delta\lambda_m = 18$ nm. This is near the value of 20 nm typically observed for normal red blood cells in experiments. FIGS. 4a and 4b show shifts of 25 nm and 26 nm, respectively, for two healthy blood samples.

The amount of the mode spectral shift $\Delta\lambda.m$ is also a function of the filling function, i.e., the thickness of the cell under investigation with respect to the thickness, or channel depth, of the cavity. Ideally, the channel depth should correspond closely to the thickness of the cell. The goal is to maximize the fraction of the total optical mode volume occupied by the cell. A fraction of the mode volume is resident within the solid materials which form the cavity walls. The majority of the mode volume lies within the cavity. A cell that fills the entire cavity will have the optimum mode filling fraction. Under this condition, the spectral shift in the transverse modes will be maximum and the sensitivity of the detection of the mode shift will be optimized. Cavities with larger channel dimensions will result in lower spectral shifts and lower detector sensitivity. Cavities with smaller channel dimensions will not allow the cells to pass easily through the channel. Fortunately, most normal and anemic blood cells have a thickness on the order or 2 to 3 microns, so a cavity thickness of 2 microns provides optimal filling for most cells.

Figure 5A:
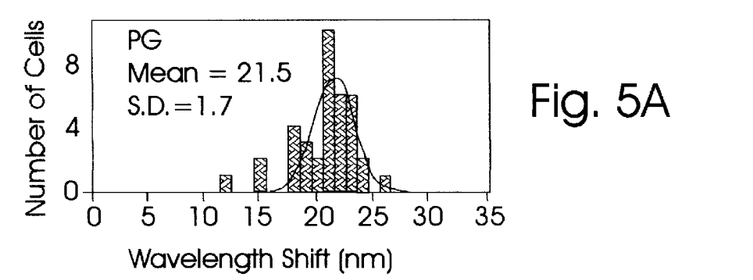
FIGS. 5a and 5b show histograms of wavelength shifts of normal and anemic blood.
Figure 5B:
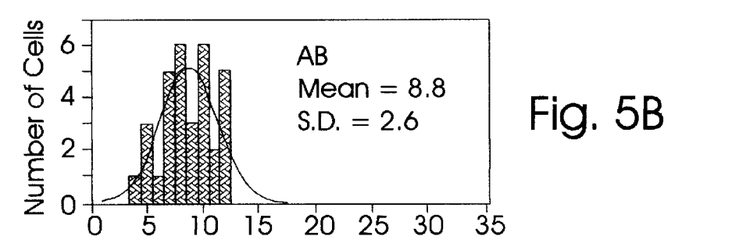
Figure 6A:
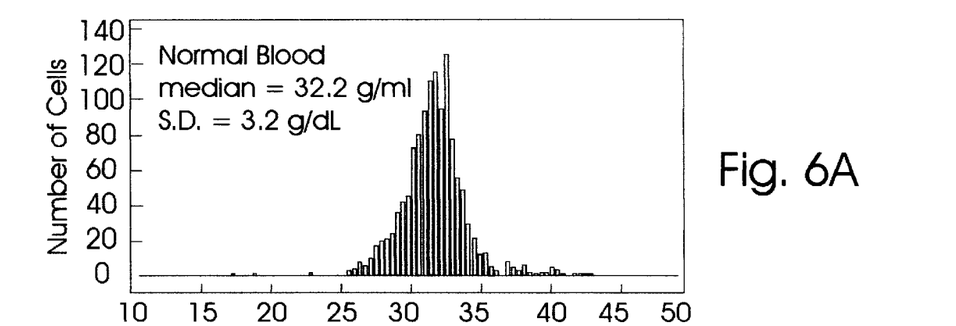
FIGS. 6a and 6b show histograms of hemoglobin concentration of normal and anemic blood.
Figure 6B:
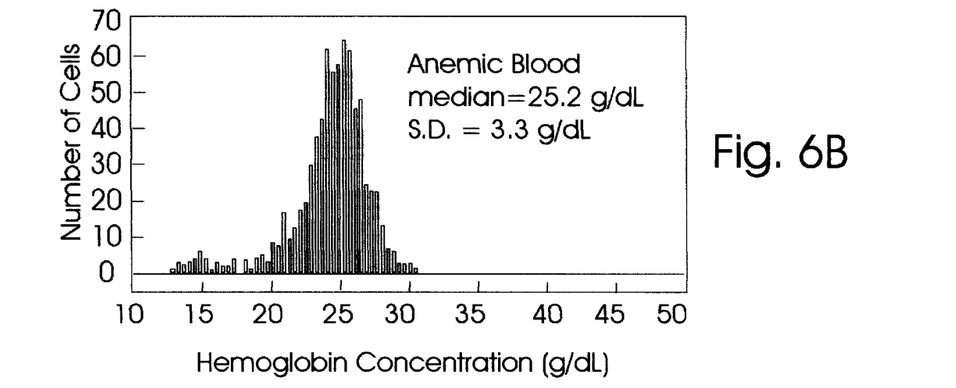

Alternately, the hemoglobin concentration can be determined from the mode shift as $C = \Delta n_1/\alpha$ in g/dL. FIGS. 5a and 6a show histogram of such hemoglobin measurements in a number of red cells from two individuals with normal blood, while FIGS. 5b and 6b show similar measurements from two anemic people. All blood samples were measured by standard hematology methods for reference.

For the tests of FIGS. 5a and 5b, the cavity had a sufficient cross-sectional area to hold 10's of static cells, and the tests were made by moving the laser from cell to cell. The normal red cell histogram of FIG. 5a shows a mean hemoglobin concentration of about 34 g/dL and a standard deviation of 7%. In contrast, the anemic red cell histogram in FIG. 5b shows a much lower mean concentration of 13 g/dL and a standard deviation of 25%. From this information, it is clearly seen that for the 2 micron thick test cavity, a shift of the fundamental transverse mode of approximately 18 nm or greater indicates a cell with normal hemoglobin, while a shift of approximately 13 nm or less indicates a cell of an a person with anemia. Similar results are obtained from blood samples from other people.

The test cavity for the histograms of FIGS. 6a and 6b was a narrow flow channel similar to the embodiment of FIG. 2, with a thickness of 3 microns. Because this cavity was not filled as completely by each cell as the 2 micron cavity of FIGS. 5a and 5b, the shifts of the transverse peaks were not as great as in the previous test. However, the advantageous flow design allowed a much greater number of cells to be quickly measured. In addition, these curves are plotted as a function of hemoglobin concentration, as the measured wavelength shifts have been converted using the relationship of Eq. 9. The curves indicate that while measurement of an individual cell could provide an ambiguous reading if it was between 25 and 30 g/dL for this setup, the measurement of just a few cells should provide a statistically accurate determination of hemoglobin concentration.

In order to determine cell lysing, whole blood samples were diluted with phosphate buffered salt solution and fed into the microbridge laser cavity by a micropipette. The blood fluid wicked into the microcavity and a significant fraction of the cells became attached to the surfaces of the glass or semiconductor. In this stationary condition, water with a low concentration of ions, such as deionized water, was wicked into the microbridge using a fused silica microcapillary. The rate of water transfer into the cavity was characterized in separate dye injection experiments. Typical times for water capillarity/diffusion across the 5 mm bridge were about 50 seconds depending on the conditions of the microcavity surfaces.

The cells were observed to lyse after the injection of water. Sequential images of the lysing cells were recorded by both video microscopy and laser scanning confocal microscopy. In the video images, the cell boundaries appear as dark rings around a light background. Within about 20 seconds, the cell boundaries lose contrast and the cells disappears. Changes from the initial state of high contrast to the final state of near invisibility occur in about 20 seconds as in the video image. The start of the lysing process was observed to vary from seconds to several minutes after water injection, depending on the location of the cell relative the injection point.

Figure 7:
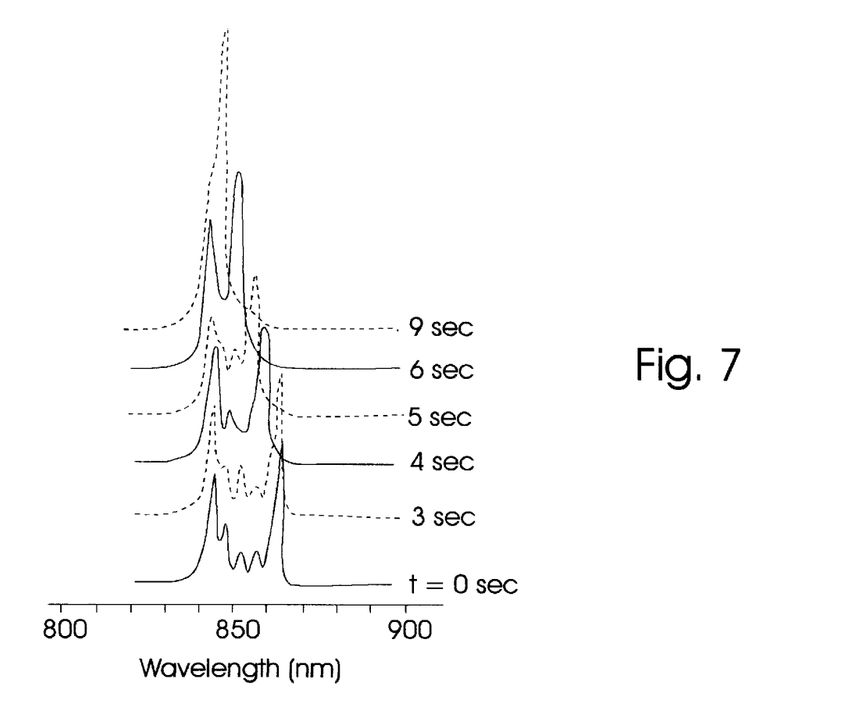
FIG. 7 shows the change in spectra of lysing red blood cells.

Typical spectra for red blood cells lysing in the cavity are displayed in FIG. 7. Initially, the spectrum is static and comprises a peak due to the bare-fluid mode and series of cell modes at longer wavelength. The cell mode spectrum exhibits 3 basic features, each related to the cell structure and composition. First, the displacement of the longest wavelength mode from the fluid mode represents the index difference between the fluid (diluted blood plasma) the cell (principally a hemoglobin solution). This difference increases with hemoglobin concentration. Second, the relative spacing of the modes is representative of the size of the cell. Large mode spacings corresponds to small cell diameter. Finally, the envelope of modal intensities is representative of the cell shape. Cells with high biconcavity have spectra with significant intensity in the first and higher overtones. Spherical cells have spectra with dominant fundamental modal intensity.

Under lysing, the spectra undergo dramatic changes that last for 10 to 20 seconds. There are four salient features that implore description and explanation. Initially, the right-most peak shifts continuously to shorter wavelengths. The shifting peak is not a mode hopping to shorter wavelengths. As the peak moves continuously as a function of time, there is no residual intensity at wavelengths longer than that of the peak. The shift represents a true displacement of a low order mode (either the fundamental or the first overtone). Secondly, the intensity of that peak increases two- or threefold during the shift. Thirdly, during the shift the shorter wavelength peaks appear to remain stationary with little change in position or intensity. Finally, the shift continues until that peak merges with the bare fluid mode.

Figure 8:
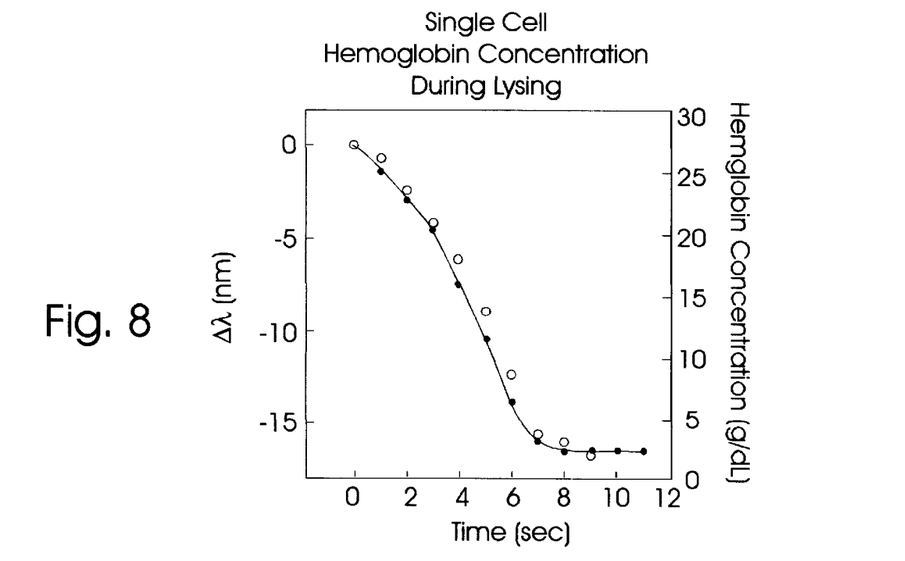
FIG. 8 shows a plot of peak shift and hemoglobin concentration as a function of time during lysing.

The peak shift is plotted against time in FIG. 8. The initial shift of the peak is 1 nm/s for the first several seconds, then more rapidly 3 nm/s to bring it to within a few nanometers of the bare-fluid mode. After this, the final merging requires more time to complete. In most cells the merging is complete in 5 to 10 seconds, leaving only a single bare-fluid mode in the spectra. Visual inspection of the cell under this condition reveals only a faint, nearly invisible image of the original cell with little change in diameter. The resolution of peak shift is about 0.01 nm. At initial times, this corresponds to 10 ms time resolution. Thus, the microcavity spectra are several orders of magnitude more sensitive to cell structure changes than standard optical microscopy.

A simple interpretation of the above observations is as follows. The shift of the low order mode arises from the decrease in refractive index of the cell. This can be explained by a dilution of the cell fluids (primarily hemoglobin) by the uptake of water. This is consistent with the fact that the number of modes decreases with time, which can happen only if the cell radius or refractive index decreases. Since neither the higher order spectral modes spacings increase nor the recorded images show changes in the cell diameter, the cell diameter does not decrease. Thus, the refractive index of the cell must be decreasing. Before lysing, the cell has a biconcave structure and exhibits a dominant first overtone mode in the spectra. During water uptake, the cell becomes more spherical and the fundamental mode dominates and begins shifting. Eventually, the whole cell is diluted and the fundamental and higher overtones all collapse into the bare fluid mode.

There is no evidence in the spectra or the images to support a diametrical swelling of the cell. If this were the case, the spectral mode spacing would decrease and there would be an initial red shift of the major peak (or at least a slowing of the blue shift).

The increase in mode intensity with time may result from two effects. The first is simply that a small absorption by hemoglobin occurs at the pump laser wavelength of 532 nm. Thus as the hemoglobin concentration decreases, the pump more effectively transmits to the semiconductor. Alternately, the pump spot may be larger than the cell and more optimally match the increasing modal area as the cell index decreases.

It is important to consider the effect of laser power on the cell structure. The incident power was always kept quite low (about 1 milliwatt) to avoid heating the cells. In fact, cells not exposed to water exhibited spectra that remained constant in time. The absence of any significant is mode shifts or intensity changes indicates that the heating effects are small. Under condition of very high pump powers the merging of the cell and bare fluid modes is never completed. A sharp peak, near but distinct from the fluid mode is evident. Visual inspection under this condition reveals a markedly different image. The cell image retains high contrast but is dramatically reduced in diameter. The diameter of these "dwarf cells" are two to three times smaller than the original. The formation of these shrunken cells with intact membranes is likely due to heating.

It is also noted that the measurements disclosed herein were taken at room temperature and underestimate the actual lysis at 37° C. in the body.

The particular sizes and equipment discussed above are cited merely to illustrate a particular embodiment of this invention. It is contemplated that the use of the invention may involve components having different sizes and shapes as long as the principle of using a microcavity to measure blood spectra, and determine characteristics of the blood, is followed. It is intended that the scope of the invention be defined by the claims appended hereto.

What is claimed is:

1. A method for determining hemoglobin comprising:
   determining the wavelength of a longitudinal mode of a laser microcavity containing only a liquid;
   determining the wavelength of a transverse mode of said longitudinal mode of the laser microcavity containing a red blood cell in the liquid;
   determining hemoglobin concentration as a direct function of the difference between the wavelength of the longitudinal mode and the transverse mode.

2. The method of claim 1 wherein the wavelength of the transverse mode is determined from the spectrum of a microcavity containing a red blood cell.

3. The method of claim 1 wherein said difference is on the order of 20 nm for a hemoglobin concentration on the order of 35 g/dL.

4. The method of claim 1 wherein the transverse mode is the fundamental transverse mode.

5. The method of claim 1 wherein said microcavity comprises a tubular passage in an analysis region between two spaced mirrors, said method further comprising: supplying liquid at one end of said passage and removing liquid from an opposite end of said passage; and controlling the flow of liquid through said passage.

6. The method of claim 1 further comprising introducing a second liquid into the cavity to cause lysing of the cell; and
   determining cell fragility as a function of a decrease in said difference as a function of time.

7. The method of claim 6 wherein said second liquid is water.

8. The method of claim 6 wherein the transverse mode is the fundamental transverse mode.

9. The method of claim 8 wherein said difference approaches zero as the hemoglobin concentration is reduced by dilution of the cell.

* * * * *